United States Patent
Belt et al.

(10) Patent No.: US 10,130,341 B2
(45) Date of Patent: *Nov. 20, 2018

(54) IMAGING SYSTEM FOR IMAGING A PERIODICALLY MOVING OBJECT

(71) Applicant: KONINKLIJKE PHILIPS N.V., Eindhoven (NL)

(72) Inventors: Harm Jan Willem Belt, Weert (NL); Steven Antonie Willem Fokkenrood, S'Hertogenbosch (NL); Fei Zuo, Eindhoven (NL); Alexander Franciscus Kolen, Eindhoven (NL); Szabolcs Deladi, Veldhoven (NL); Godefridus Antonius Harks, Rijen (NL)

(73) Assignee: Koninklijke Philips N.V., Eindhoven (NL)

( * ) Notice: Subject to any disclaimer, the term of this patent is extended or adjusted under 35 U.S.C. 154(b) by 943 days.

This patent is subject to a terminal disclaimer.

(21) Appl. No.: 14/383,140

(22) PCT Filed: Mar. 20, 2013

(86) PCT No.: PCT/IB2013/052225
§ 371 (c)(1),
(2) Date: Sep. 5, 2014

(87) PCT Pub. No.: WO2013/140358
PCT Pub. Date: Sep. 26, 2013

(65) Prior Publication Data
US 2015/0011883 A1    Jan. 8, 2015

Related U.S. Application Data

(60) Provisional application No. 61/614,550, filed on Mar. 23, 2012.

(51) Int. Cl.
*A61B 8/08* (2006.01)
*A61B 8/00* (2006.01)
(Continued)

(52) U.S. Cl.
CPC ............ *A61B 8/5207* (2013.01); *A61B 8/461* (2013.01); *A61B 8/5276* (2013.01);
(Continued)

(58) Field of Classification Search
CPC ..... A61B 8/5276; A61B 8/486; A61B 8/0858; A61B 8/465; A61B 8/12; A61B 8/0883;
(Continued)

(56) References Cited

U.S. PATENT DOCUMENTS 5,090,413 A * 2/1992 Yoshioka ................. A61B 8/06
600/441
5,515,856 A    5/1996 Olstad et al.
(Continued)

FOREIGN PATENT DOCUMENTS

EP    1806594 A2    7/2007
EP    2082688 A1    7/2009
(Continued)

OTHER PUBLICATIONS

Shung, "Diagnostic Ultrasound: Imaging and Blood Flow Measurements". Taylor & Francis. 2006. chapter 4, pp. 79-101.*
(Continued)

*Primary Examiner* — Jennifer Dieterle
*Assistant Examiner* — Colin T Sakamoto

(57) ABSTRACT

The invention relates to an imaging system for imaging a periodically moving object. An assigning unit (18) assigns ultrasound signals like A-lines to motion phases based on a provided phase signal, wherein an ultrasound images generation unit (19) generates several ultrasound images like gated M-mode images for the different motion phases based
(Continued)

on the ultrasound signals assigned to the respective motion phase. The ultrasound images are temporally consecutively displayed on a display unit (21) for showing the periodic movement of the object (24). The resulting dynamic, movie-like image of the object allows a user like a physician to more reliably determine properties of the object like a thickness of a tissue wall, in particular, during an ablation procedure. The imaging system is therefore particularly useful for monitoring cardiac ablation procedures.

14 Claims, 12 Drawing Sheets

(51) Int. Cl.
  A61B 8/12 (2006.01)
  A61B 18/14 (2006.01)
  A61B 18/00 (2006.01)
  A61B 90/00 (2016.01)

(52) U.S. Cl.
  CPC ............ *A61B 8/5284* (2013.01); *A61B 8/543* (2013.01); *A61B 8/12* (2013.01); *A61B 8/486* (2013.01); *A61B 18/1492* (2013.01); *A61B 2018/00577* (2013.01); *A61B 2090/3784* (2016.02)

(58) Field of Classification Search
  CPC ..... A61B 8/5284; A61B 8/5207; A61B 8/461; A61B 8/543
  See application file for complete search history.

(56) References Cited

U.S. PATENT DOCUMENTS

| | | | |
|---|---|---|---|
| 5,916,168 A * | 6/1999 | Pedersen | A61B 8/08 128/916 |
| 6,224,553 B1 * | 5/2001 | Nevo | A61B 8/08 600/437 |
| 6,558,325 B1 | 5/2003 | Pang et al. | |
| 7,606,402 B2 * | 10/2009 | Heimdal | A61B 8/00 382/128 |
| 7,674,228 B2 | 3/2010 | Williams et al. | |
| 8,317,714 B2 * | 11/2012 | Hendriks | A61B 5/021 600/440 |
| 2005/0033123 A1 | 2/2005 | Gardner et al. | |
| 2007/0066898 A1 * | 3/2007 | Hendriks | A61B 5/021 600/437 |
| 2009/0318812 A1 | 12/2009 | Suijver et al. | |
| 2010/0168573 A1 * | 7/2010 | Sherrill | A61B 8/0883 600/440 |
| 2010/0185088 A1 * | 7/2010 | Perrey | A61B 8/08 600/443 |
| 2011/0044522 A1 * | 2/2011 | Fancourt | G06T 7/2033 382/131 |
| 2011/0251529 A1 | 10/2011 | Petruzzello et al. | |
| 2012/0004547 A1 | 1/2012 | Harks et al. | |

FOREIGN PATENT DOCUMENTS

| | | |
|---|---|---|
| JP | S58180138 A | 10/1983 |
| JP | 2009119250 A | 6/2009 |

OTHER PUBLICATIONS

Afonso, V. et al. "ECG beat detection using filter banks" IEEE Transactions on Biomedical Engineering, vol. 46, No. 2, pp. 192 to 202 (1999).

Ketterling, J. et al. "Prospective ECG-gated Mouse Cardiac Imaging with a 34-MHz Annular Array Transducer". National Institute of Health. IEEE Trans Ultrason Ferroelectr Freq Control. Jul. 2009; 56(7): 1394-1404.

* cited by examiner

IMAGING SYSTEM FOR IMAGING A PERIODICALLY MOVING OBJECT

CROSS-REFERENCE TO PRIOR APPLICATIONS

This application is the U.S. National Phase application under 35 U.S.C. § 371 of International Application Serial No. PCT/IB2013/052225, filed on Mar. 20, 2013, which claims the benefit of U.S. Application Ser. No. 61/614,550, filed on Mar. 23, 2012. These applications are hereby incorporated by reference herein.

FIELD OF THE INVENTION

The invention relates to an imaging system, an imaging method and an imaging computer program for imaging a periodically moving object.

BACKGROUND OF THE INVENTION

US 2012/004547 A1 discloses a monitoring apparatus for monitoring an ablation procedure. The monitoring apparatus comprises an ultrasound image providing unit for providing an M-mode image of cardiac tissue during an ablation procedure such that a physician can control the ablation procedure based on the M-mode image.

SUMMARY OF THE INVENTION

It is an object of the present invention to provide an imaging system, an imaging method and an imaging computer program for imaging a periodically moving object, which visualize ultrasound data of the object in an alternative way such that, for instance, an ablation procedure can be controlled with improved quality based on the visualization, despite the periodic movement.

In a first aspect of the present invention an imaging system for imaging a periodically moving object is presented, wherein the imaging system comprises:
- an ultrasound signals providing unit for providing ultrasound signals of the object for different times,
- a phase signal providing unit for providing a phase signal being indicative of motion phases of a periodic movement of the object at the different times,
- an assigning unit for assigning the ultrasound signals to the motion phases based on the provided phase signal,
- an ultrasound images generation unit for generating several ultrasound images for the different motion phases, wherein an ultrasound image for a motion phase is generated based on the ultrasound signals assigned to the respective motion phase, and
- a display control unit for controlling a display unit, wherein the display control unit is adapted such that the generated ultrasound images are temporally consecutively displayed on the display unit for showing the periodic movement of the object.

Since the ultrasound images generation unit generates ultrasound images for motion phases based on the ultrasound signals assigned to the respective motion phase, wherein these ultrasound images are temporally consecutively displayed on the display unit, a dynamic, movie-like image of the periodically moving object can be shown, instead of a conventional static ultrasound image, in particular, instead of a conventional static M-mode image. This dynamic, movie-like image of the object allows a user like a physician to more reliably determine properties of the object like a thickness of a tissue wall, which may be ablated by the user. This in turn allows a user to improve the quality of controlling an application of energy to the object, in particular, an ablation of a tissue wall, based on ultrasound data.

The ultrasound signals providing unit is preferentially adapted to provide A-lines of the object as the ultrasound signals. The ultrasound signals providing unit is preferentially further adapted to apply an envelope detection procedure on the A-lines and to provide the resulting A-line envelopes as the ultrasound signals. In particular, the ultrasound images generation unit is adapted to generate several M-mode images for the different motion phases, wherein an M-mode image for a motion phase is generated from the A-lines, in particular, the A-line envelopes, assigned to the respective motion phase. The several M-mode images generated for the different motion phases can be regarded as being gated M-mode images.

Preferentially, the ultrasound signals are provided temporally consecutively, wherein, if an actual ultrasound signal has been provided, the actual ultrasound signal can be assigned to a corresponding motion phase and the actual ultrasound signal can then be used to update the ultrasound image, which corresponds to the motion phase, to which the actual ultrasound signal has been assigned. For instance, if the ultrasound signals are A-lines and if the generated ultrasound images are gated M-mode images, the respective actual A-line can be assigned to a motion phase, wherein then the actual A-line can be appended to the gated M-mode image, which corresponds to the motion phase, to which the actual A-line has been assigned.

The ultrasound signals providing unit can be an ultrasound signal measuring unit for measuring the ultrasound signals of the object for different times, in particular, for measuring A-lines. Thus, the ultrasound signals providing unit can comprise one or several ultrasound transducers for sending ultrasound pulses out to and into the object and for receiving dynamic echo series after the ultrasound pulses have been reflected by the object. The ultrasound signal, in particular, the respective A-line, is then generated depending on the received dynamic echo series. The object is preferentially tissue, especially cardiac tissue, wherein the ultrasound pulses are sent into the cardiac tissue and the dynamic echo series are received from the cardiac tissue such that the generated ultrasound signal is indicative of properties of the cardiac tissue in different depths.

The ultrasound signals providing unit can also be a storing unit, in which the already measured ultrasound signals are stored, or the ultrasound signals providing unit can be a receiving unit for receiving the ultrasound signals and for providing the received ultrasound signals.

The phase signal providing unit can be a phase signal measuring unit for measuring a phase signal being indicative of motion phases of a periodic movement of the object at the different times, at which the ultrasound signals have been measured. However, also the phase signal providing unit can be a storing unit, in which the measured phase signal is stored already, or a receiving unit for receiving the measured phase signal and for providing the received phase signal.

The imaging system can therefore comprise measurement components for measuring ultrasound signals and/or phase signals, or the imaging system can be a computing system, which does not comprise measuring components, wherein in the latter case the ultrasound signals providing unit and the phase signal providing unit are storing units or receiving units, respectively, of the computer system.

The display control unit is preferentially adapted to determine a repetition rate of displaying the generated ultrasound images from the provided phase signal and to control the display unit to display the generated ultrasound images temporally consecutively with the determined repetition rate. The repetition rate defines how often an ultrasound image of a same motion phase is displayed in a time interval. The resulting frame rate, which can be defined as the total number of images shown in a time interval, is defined by the repetition rate multiplied by the number of motion phases, for which an ultrasound image has been generated.

In a preferred embodiment the display control unit is adapted to determine a motion rate of the periodic movement of the object from the provided phase signal and to determine the repetition rate depending on the motion rate. For instance, the repetition rate can be equal to the motion rate, in particular, the last motion rate, or can be an average of several motion rates determined for several motion periods of the periodic movement. Thus, the frame rate can be such that N consecutive ultrasound images are shown in a time period T which is equal to one cycle period of the motion, if the motion period is subdivided into N motion phases. Since the repetition rate preferentially depends on the motion rate, it can vary depending on a possible variation of the motion rate. For instance, if the motion rate increases, also the repetition rate may increase, and, if the motion rate decreases, also the repetition rate may decrease. The motion rate is, for example, a heartbeat rate or a respiratory rate.

It is preferred that the imaging system is adapted to continuously provide ultrasound signals, assign the ultrasound signals to the motion phases, generate the ultrasound images and display the generated ultrasound images, wherein the ultrasound images generation unit is adapted to, after initial ultrasound images have been generated, update the ultrasound images based on the actually provided ultrasound signals, and the display control unit is adapted to control the display unit to display the updated ultrasound images temporally consecutively for showing an updated periodic movement of the object. In particular, the ultrasound signals providing unit is adapted to continuously provide A-lines as the ultrasound signals, wherein the images generation unit is adapted to generate gated M-mode images as the ultrasound images, wherein, after initial gated M-mode images have been generated, the gated M-mode images are updated by appending actually provided A-lines and wherein the display control unit is adapted to control the display unit to display the updated gated M-mode images temporally consecutively for showing an updated periodic movement of the object. The shown dynamic, movie-like image of the object can therefore consider the actual properties of the object as sensed by the ultrasound, i.e. the shown dynamic, movie-like image can continuously be modified in accordance with the actually provided ultrasound signals, in particular with the actually provided A-lines.

The assigning unit can be adapted to subdivide a motion period into the motion phases such that they have different durations depending on the phase signal. Thus, the duration of the motion phases can be adapted to the respective motion of the object such that the quality of the shown dynamic, movie-like image is further improved. For instance, motion phases, in which the movement of the object is smaller, can have a duration being larger than a duration of another moving phase, in which the movement of the object is larger. In particular, if the phase signal is a cardiac motion signal, the assigning unit can be adapted such that the duration of a motion phase including the diastole, when the heart muscles are at rest, is larger than the duration of a motion phase including the systole.

In an embodiment the ultrasound signals providing unit is adapted to provide A-lines as the ultrasound signals, the assigning unit is adapted to assign the A-lines to the motion phases based on the provided phase signal, and the images generation unit is adapted to generate M-mode images for the different motion phases as the ultrasound images based on the respective assigned A-lines, wherein the width of the A-lines of at least one motion phase is modified such that for different motion phases the width of the A-lines used for generating the respective M-mode image is similar. Thus, the images generation unit can be adapted to re-scale a group of A-lines belonging to a certain motion phase, in order to match the size of a group of A-lines belonging to the other motion phases, so that all motion phases end up to produce the same amount of appended data in the gated M-mode images. Such a resizing ensures that the different gated M-mode images have the same size such that, if the gated M-mode images are displayed temporally consecutively on the display unit for showing the periodic movement of the object, a flickering of the shown movement caused by differently sized gated M-mode images can be prevented.

In an embodiment the assigning unit is adapted to assign the ultrasound signals to motion phases of a respective motion period, after the respective motion period has been completed. Since after the respective motion period has been completed, the duration of the respective motion period is known, the different motion phases can accurately be determined by subdividing the respective motion period into the motion phases. Correspondingly, the assignment of the ultrasound signals to the motion phases can be very accurately, thereby leading to a further improved quality of the finally shown dynamic image of the object.

In a further embodiment the assigning unit is adapted to assign the ultrasound signals of a motion period of the object to the motion phases based on the phase signal provided for a previous motion period. Thus, the ultrasound signals can be assigned to a motion phase, before the actual motion period has been completed. This allows assigning the ultrasound signals to the movement phases with very low latency such that the ultrasound images generation unit can generate actual ultrasound images for the different motion phases, which include the last provided ultrasound signals, with very low latency. For instance, temporally consecutively A-lines can be provided as the ultrasound signals, wherein the actual provided A-line can be assigned to a movement phase based on a subdivision of the previous motion period into movement phases, wherein the actual A-line can be appended to the gated M-mode image, which corresponds to the movement phase to which the actual A-line has been assigned.

The assigning unit can be adapted to reassign the ultrasound signals of a respective motion period of the object, which have been assigned to the motion phases based on the phase signal for a previous motion period, based on the phase signal of the respective motion period, after the respective motion period has been completed, wherein the ultrasound images generation unit is adapted to generate the ultrasound images based on the reassigned ultrasound signals and wherein the display control unit is adapted to control the display unit to display the generated ultrasound images. The initial approximate assignment of the ultrasound signals to the motion phases, which were based on a previous motion period, can therefore be corrected, after the respective motion period has been completed, thereby providing an accurate assignment of the ultrasound signals to the motion phases and, thus, a high quality dynamic image of the object, wherein the actually acquired, latest ultrasound signals can still be shown with very low latency.

The phase signal providing unit can be adapted to provide several phase signals being indicative of motion phases of different kinds of periodic movements of the object, wherein the assigning unit can be adapted to assign the ultrasound signals to a combination of motion phases of the different kinds of periodic movements based on the provided several phase signals, wherein the ultrasound images generation unit is adapted to generate several ultrasound images for the different combinations, wherein an ultrasound image for a combination is generated based on the ultrasound signals assigned to the respective combination. The different combinations of the motion phases of the different kinds of periodic movements of the object occur temporally consecutively, wherein the display control unit is adapted to control the display unit such that the generated ultrasound images are temporally consecutively displayed on the display unit in accordance with the temporal sequence defined by the respective combinations. This allows showing a dynamic image of the object, which not only considers a single kind of periodic movement, but several kinds of periodic movements, which may lead to a further improved visualization of the periodically moving object.

In a preferred embodiment the imaged object is a region of a living being like a tissue wall, wherein the phase signal providing unit is adapted to provide at least one of a cardiac motion signal being indicative of cardiac motion and a respiratory motion signal being indicative of respiratory motion as the phase signal. The phase signal providing unit can also be adapted to provide at least one of an atrium motion signal being indicative of atrium motion and a ventricle motion signal being indicative of ventricle motion as the phase signal.

The cardiac motion signal can be an electrocardiography signal from, for example, electrocardiography surface leads attached to the breast of the living being. Alternatively or in addition, the ultrasound signals providing unit can be integrated in a catheter, in particular, into a tip of the catheter, wherein also an electrode for measuring a cardiac signal can be integrated in the catheter, especially in the catheter tip. The phase signal providing unit can also be pulse oximeter detector that can be clipped onto a finger or an earlobe, wherein the pulse oximeter detector provides the cardiac signal. The respiratory motion signal can be, for instance, an airflow signal produced by a tracheal intubation device. A respiratory signal may also be generated from a bio-impedance signal that may be measured via electrocardiography electrodes.

The phase signal providing unit can also be adapted to determine the phase signal from the ultrasound signals and to provide the determined phase signal. In particular, the phase signal, which can also be regarded as being a trigger signal, can be taken from an A-line envelope by using, for instance, a Fourier analysis or a correlation analysis in a lateral direction, i.e. in the direction of the temporal axis of the M-mode image formed by the A-line envelopes. Thus, the phase signal may be determined without necessary requiring a further measuring device like an electrocardiograph, which may simplify the handling of the imaging system.

The imaging system preferentially comprises a sensing probe, in which the ultrasound signals providing unit and an energy application unit for applying energy to the object are integrated. The sensing probe is preferentially a catheter, in which at least a part of the ultrasound signals providing unit, for instance, one or several ultrasound transducers, and at least a part of the energy application unit, for instance, an ablation electrode, are integrated. Thus, a single sensing probe may be provided, which can be used for applying energy to the object, in particular, for performing a cardiac ablation procedure, and for monitoring the application of the energy by using ultrasound.

In a further aspect of the present invention an imaging method for imaging a periodically moving object is presented, wherein the imaging method comprises:

providing ultrasound signals of the object for different times by an ultrasound signals providing unit, providing a phase signal being indicative of motion phases of a periodic movement of the object at the different times by a phase signal providing unit, assigning the ultrasound signals to the motion phases based on the provided phase signal by an assigning unit, generating several ultrasound images for the different motion phases by an ultrasound images generation unit, wherein an ultrasound image for a motion phase is generated based on the ultrasound signals assigned to the respective motion phase, controlling a display unit by a display control unit, wherein the display control unit is adapted such that the generated ultrasound images are temporally consecutively displayed on the display unit for showing the periodic movement of the object.

In a further aspect of the present invention a computer program for imaging a periodically moving object is presented, wherein the computer program comprises program code means for causing an imaging apparatus as defined in claim 1 to carry out the steps of the imaging method as defined in claim 14, when the computer program is run on a computer controlling the imaging apparatus.

It shall be understood that the imaging system of claim 1, the imaging method of claim 14 and the computer program claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
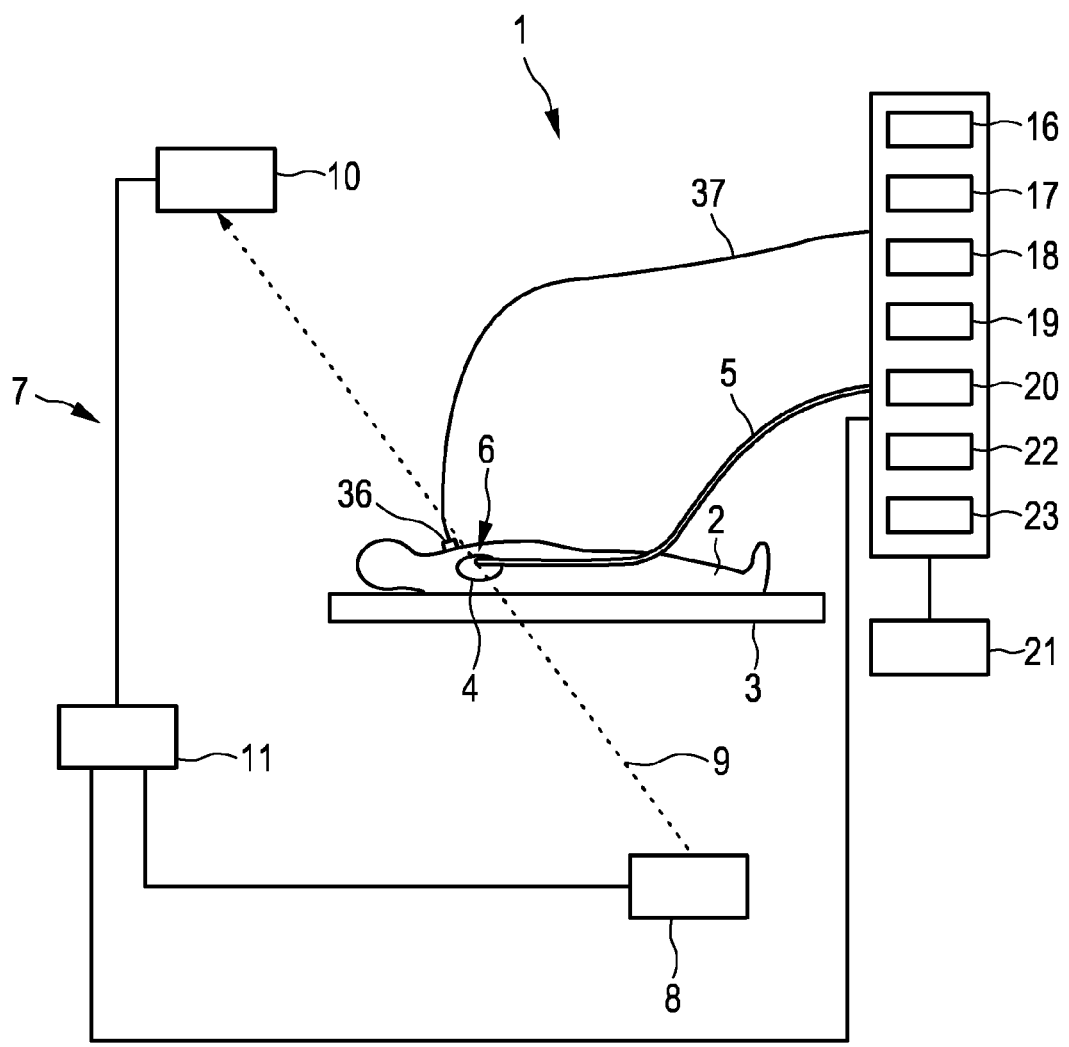
FIG. 1 shows schematically and exemplarily an embodiment of an imaging system for imaging a periodically moving object.
Figure 2:
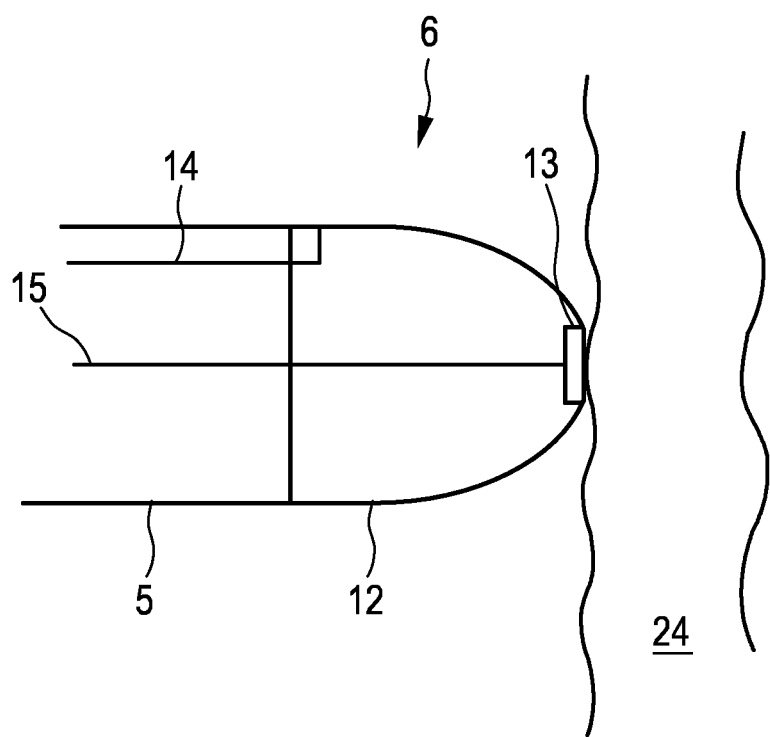
FIG. 2 shows schematically and exemplarily an embodiment of a tip of a catheter of the imaging system.

FIG. 1 shows schematically and exemplarily an imaging system 1 for imaging a periodically moving object. In this embodiment, the periodically moving object is a tissue wall of a heart 4 of a person 2 lying on a table 3. The imaging system 1 comprises a catheter 5 with a catheter tip 6, which is shown in more detail in FIG. 2.

The catheters tip 6 comprises an ultrasound transducer 13, which is connected to an ultrasound control unit 16 for controlling the ultrasound transducer 13 via an electrical connection 15 like an insulated wire. The ultrasound transducer 13 and the ultrasound control unit 16 form an ultrasound signals providing unit for providing ultrasound signals of the tissue wall 24 for different times. In particular, the ultrasound transducer 13 and the ultrasound control unit 16 are adapted to send ultrasound pulses into the tissue wall 24, to receive echo series after the ultrasound pulses have been reflected by the tissue wall 24 and to generate A-lines depending on the received echo series. The ultrasound signals providing unit 13, 16 acquires therefore temporally consecutively A-lines for providing ultrasound signals of the tissue wall 24 for different times, i.e. to each A-line a time can be assigned being the time at which the respective ultrasound pulse has been sent and received by the ultrasound signals providing unit 13, 16.

The ultrasound signals providing unit 13, 16 can preferentially be operated in an ultrasound transmission mode and in an ultrasound reception mode. In the ultrasound transmission mode the ultrasound control unit 16 provides an electrical pulse to the ultrasound transducer 13, which is a piezoelectric transducer and which converts the electrical pulse to a high-frequency sound wave, i.e. to ultrasound, which propagates through the tissue wall 24 and which is reflected and/or scattered, where the tissue wall 24 is inhomogeneous. In the ultrasound reception mode the reflected and/or scattered high-frequency sound wave from the tissue wall 24 is captured using the same piezoelectric transducer, which converts it in an electrical signal, which is transmitted to the ultrasound control unit 16. In another embodiment the catheter tip 6 can also comprise several ultrasound transducers, wherein all ultrasound transducers can be adapted to send ultrasound into the tissue wall and to receive reflected and/or scattered ultrasound from the tissue wall or wherein at least one of the ultrasound transducers is adapted to send the ultrasound into the tissue wall and at least one other ultrasound transducer is adapted to receive the reflected and/or scattered ultrasound.

Figure 3:
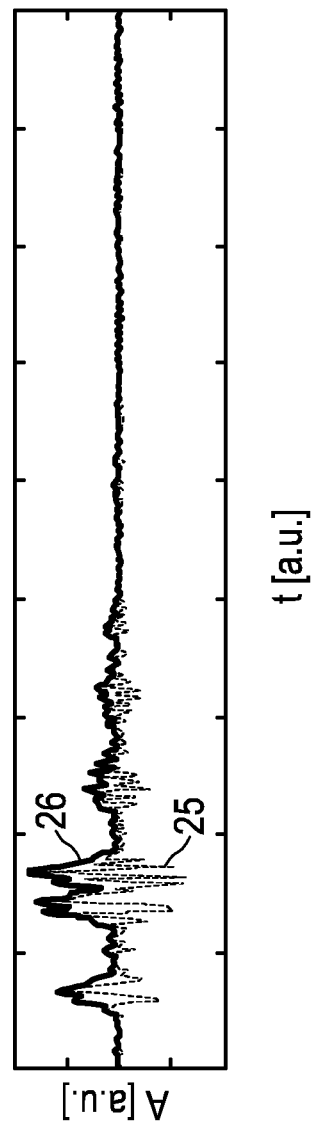
FIG. 3 shows schematically and exemplarily an A-line and an A-line envelope provided by the imaging system.

The A-lines are preferentially pre-filtered by the ultrasound control unit 16 to remove noise and disturbances, thereby providing a pre-filtered A-line per transmitted ultrasound pulse. A resulting A-line 25 is schematically and exemplarily shown in FIG. 3, in which the amplitude A in arbitrary units is shown depending on the time t in arbitrary units.

The ultrasound signals providing unit 13, 16, i.e. specifically the ultrasound control unit 16, is further adapted to apply an envelope detection procedure on the A-lines and to provide the resulting A-line envelopes as the ultrasound signals. The envelope detection procedure transforms a DC-free A-line into a non-negative amplitude signal, which may also be regarded as being a non-negative intensity or contrast signal. Such an A-line envelope 26 is schematically and exemplarily shown in FIG. 3. The ultrasound control unit 16 can be adapted to apply further post-processing procedures to the A-lines like a contrast enhancement procedure for improving visualization.

The imaging system 1 further comprises a phase signal providing unit 17, 36, 37 for providing a phase signal being indicative of motion phases of a periodic movement of the tissue wall 24 at the different times. In this embodiment the phase signal providing unit comprises an electrocardiography measurement unit 17 which measures an electrocardiography signal via electrodes 36 attached to the person's breast and via an electrical connection 37 like an insulated electrical wire, wherein the measured electrocardiography signal is provided as the phase signal.

The imaging system 1 further comprises an assigning unit 18 for assigning the ultrasound signals to the motion phases based on the provided phase signal. In particular, the determined motion period T can be subdivided into N motion phases, wherein to each A-line envelope the respective motion phase can be assigned. The assigning unit 18 can be adapted to determine the beat period, i.e. the motion period T, for example, as described in the article "ECG beat detection using filter banks" by V. Afonso et al., IEEE Transactions on Biomedical Engineering, volume 46, number 2, pages 192 to 202 (1999), which is herewith incorporated by reference. In particular, a heartbeat cycle, i.e. a motion period T, can be defined by the period between two subsequent R peaks of the electrocardiography signal or by any other two subsequent peaks that occur once during a heartbeat cycle. The determined heartbeat cycle, i.e. the motion period T, can be subdivided into N motion phases as schematically and exemplarily shown in FIG. 4.

Figure 4:
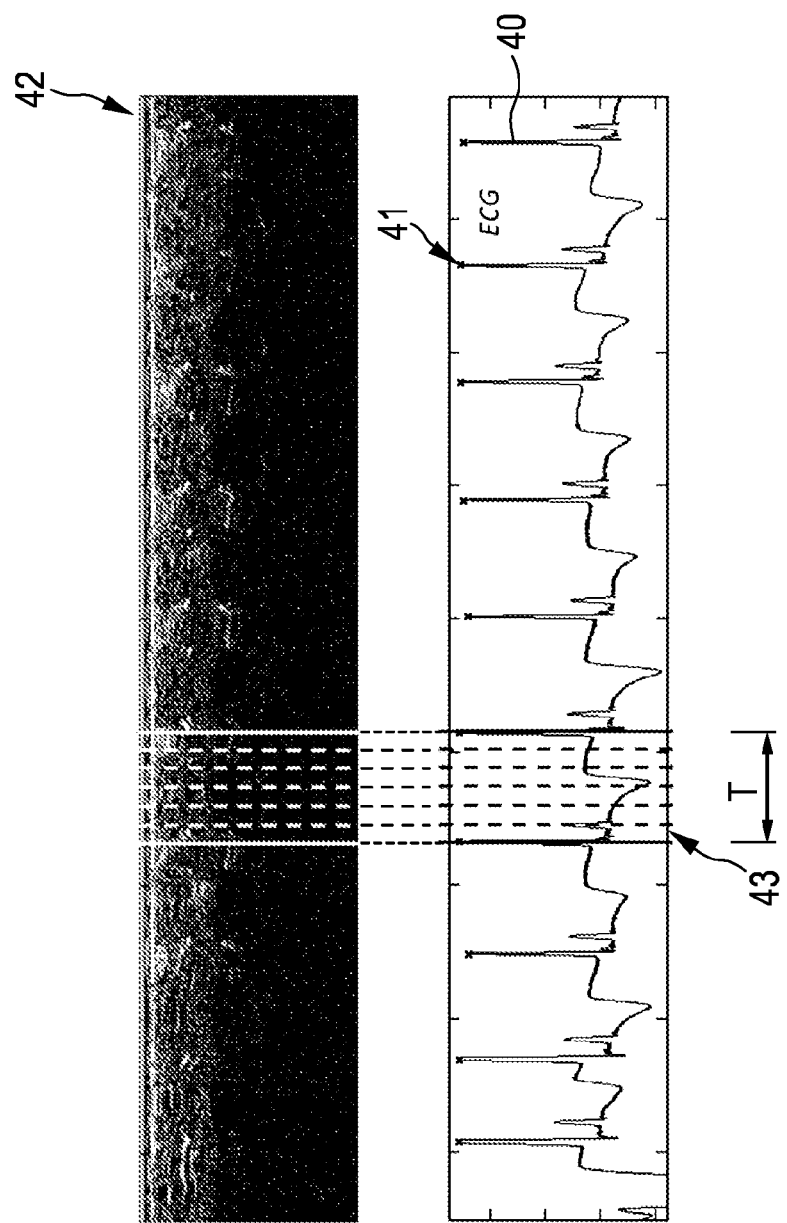
FIG. 4 shows exemplarily and schematically a cardiac phase signal and an ungated M-mode image for illustrating an assignment of A-lines to motion phases.

In FIG. 4 the upper part shows temporally consecutively the A-line envelopes, which form an M-mode image 42, and the lower part shows the provided phase signal being, in this example, an electrocardiography signal 40. The R peaks of the electrocardiography signal 40 are indicated by crosses 41. For one motion period T the subdivision into N phases is indicated. All A-line envelopes within, for instance, the region indicated in FIG. 5 by reference number 43 are assigned to the same motion phase, i.e. in this embodiment to the first motion phase. The further A-line envelopes of the period T are assigned to the respective further motion phases.

Although in this embodiment the phase signal providing unit comprises an electrocardiography measurement unit 17 for measuring an electrocardiography signal as the phase signal via electrodes 36 attached to the person's breast and via an electrical connection 37. In other embodiments a phase signal can also be provided in another way. For example, the phase signal providing unit can be adapted to take a cardiac trigger signal from an electrode inside the catheter tip, or to take the cardiac trigger signal from a conventional pulse oximeter detector that may be clipped onto a finger or an earlobe of the person. Moreover, alternatively or in addition the phase signal providing unit can be adapted to provide a breathing trigger signal, wherein this breathing trigger signal may be taken from the airflow produced by a tracheal intubation device. The breathing trigger signal may also be extracted from a bio-impedance signal measured via electrocardiography electrodes. Moreover, the phase signal providing unit may be adapted to provide a cardiac trigger signal and/or a breathing trigger signal taken from other physiological monitoring devices, in particular from remote physiological monitoring devices.

The phase signal providing unit can also be adapted to determine the phase signal from the acquired A-lines and to provide the determined phase signal.

For determining the phase signal from the acquired A-lines the generated sequence of A-line envelopes can be composed to form an M-mode image, wherein subsequent M-mode image columns contain subsequent A-line envelopes. The phase signal providing unit can be adapted to apply a Fourier analysis or a correlation analysis in the lateral direction, i.e. in the direction of the temporal axis of the M-mode image formed by the A-line envelopes, for determining the phase signal.

Figure 5:
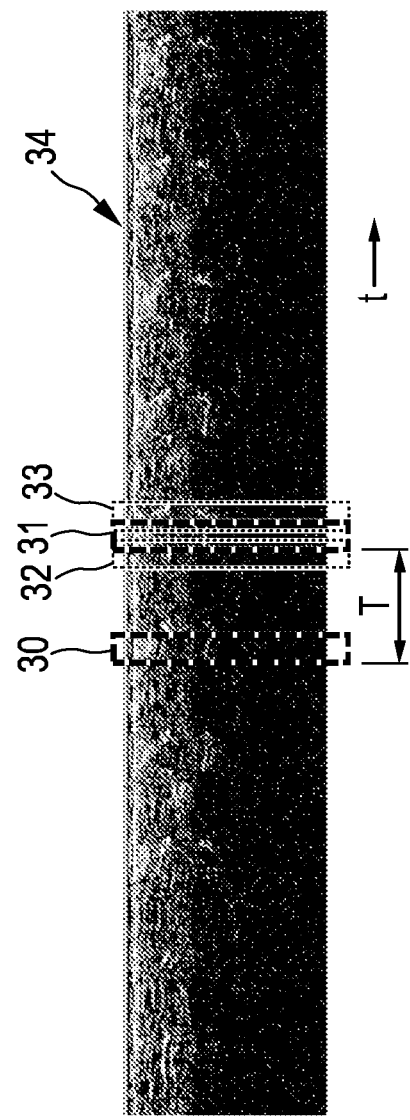
FIG. 5 shows schematically and exemplarily an ungated M-mode image for illustrating a determination of a motion period based on ultrasound image data.

FIG. 5 shows schematically and exemplarily such an M-mode image 34, wherein the lateral direction is a temporal direction indicated by t. The phase signal providing unit can be adapted to find the motion period T by using a signal correlation technique. Depending on the A-line sampling rate, i.e. the amount of A-lines per second, a set of consecutive A-line envelopes, which are indicated in FIG. 5 by the rectangle 30, is compared with several other sets of consecutive A-line envelopes at other times, which are indicated in FIG. 5 by the rectangles 31, 32, 33. The rectangle 31 defines the set of consecutive A-line envelopes, which is most similar to the set of A-line envelopes indicated by the rectangle 30. The temporal distance between these two sets of consecutive A-line envelopes defines the motion period T and, thus, the trigger signal, i.e. the phase signal. The comparison is based on a match error criterion, for instance, on the sum of absolute differences. The search area, i.e. the range of expected motion periods T, is preferentially defined by typical heartbeat rates and/or typical respiratory rates, if cardiac motion and/or respiratory motion, respectively, is considered. Typical heartbeat rates can be within a range of 40 to 140 beats per minute or within a range of 40 to 300 beats per minute for fibrillating atrium. The determined estimated motion period T is the period which minimizes the match error. The estimated motion period T at a time corresponds therefore preferentially to a minimal match error of two indicated sets of A-line envelopes. The trigger signal can be chosen to be non-zero only at the start of the respective new motion cycle having the duration T.

If the phase signal providing unit is adapted to determine the phase signal from the ultrasound signals and to provide the determined phase signal, physical connections between different hardware systems in an electrophysiology (EP) laboratory, for instance, physical connections between an electrocardiography measurement device and a cardiac ablation monitoring device, may be reduced, in particular, avoided.

The imaging system 1 further comprises an ultrasound images generation unit 19 for generating several ultrasound images for the different motion phases, wherein an ultrasound image for a motion phase is generated based on the ultrasound signals assigned to the respective motion phase. In this embodiment the ultrasound images generation unit 19 is adapted to generate for each motion phase an M-mode image, wherein an M-mode image for a motion phase is generated from the A-line envelopes assigned to the respective motion phase. The generation of the several M-mode images can be regarded as being an extraction of N gated ultrasound images from an original M-mode image which is composed of all non-gated A-line envelopes, wherein the extraction is triggered by the phase signal being synchronous with the heart beating. In other embodiments, additionally or alternatively, the phase signal can also be synchronous with the breathing motion, i.e. in an embodiment two phase signals can be provided, wherein a first phase signal is indicative of cardiac motion and a second signal is indicative of respiratory motion. In each gated ultrasound image groups of subsequent A-line envelopes are collected that belong to one particular motion phase of the motion cycle.

Figure 6:
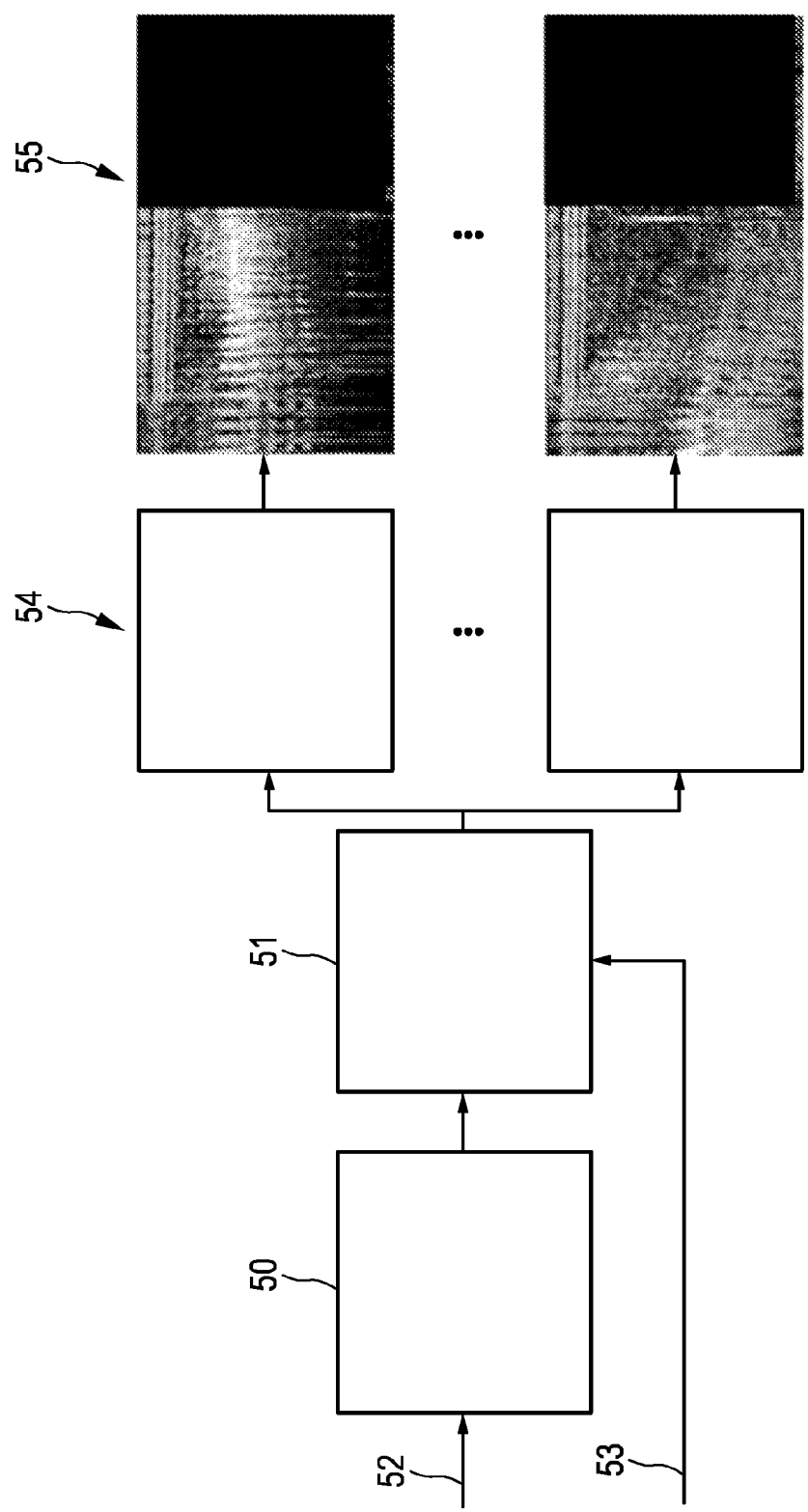
FIG. 6 shows a flowchart exemplarily illustrating a generation of gated M-mode images.

The generation of the gated M-mode images, while the A-line envelope data are generated, will exemplarily be described with reference to FIG. 6 in the following.

Raw ultrasound A-line data, which are generated by the ultrasound transducer 13, are received (52), wherein the received raw ultrasound A-line data are processed for generating filtered A-line envelope data (50). The A-line envelopes are assigned to the different motion phases (51) based on a received trigger signal (53). The A-line envelopes, which have been assigned to the different motion phases, are then appended to the respective M-mode image of the respective motion phase (54), which results in N updated M-mode images (55). Thus, for each motion phase corresponding A-line envelopes are extracted from an original M-mode image and placed behind previously extracted A-line envelopes of the same motion phase of a previous motion period. In this way an M-Mode image is subdivided into N gated images, wherein each gated image corresponds to one particular motion phase of the motion cycle.

Since the accurate division of a motion period in frames, i.e. in motion phases, which can vary in duration between motion periods, for instance, due to variations in heart rate, can only be performed after the respective motion period has finished, this generation and displaying of a gated ultrasound image may be performed with a relatively large latency. The assigning unit 18 is therefore preferentially adapted to split a motion period into motion phases based on the duration of the previous motion period such that the generation of the gated image can be started while the data arrives, wherein the assigning unit 18 can compensate/correct for potential errors due to a potential difference in duration between subsequent motion periods after the actual motion period has been finished. The ultrasound images generation unit 19 is then preferentially adapted to correct the gated ultrasound images based on the corrected assignments of the A-lines to the motion phases, in particular, by generating the gated ultrasound images again based on the corrected assignments. The preliminary assignment of the A-lines, in particular, of the A-line envelopes, based on the duration of a previous motion period generally leads only to a minor artifact of short duration because of the following correction. Since the gated images belonging to one motion period are displayed sequentially and in a cyclic manner, the just created gated images with the slightly incorrect motion period can be recomputed in the next motion phase with the correct motion period. This allows for a generation and displaying of gated ultrasound images with very low latency.

Each gated M-mode image comprises subsequent M-mode image columns which preferentially contain subsequent A-line envelopes up until the current time instance. When time progresses, the respective gated M-mode image is extending to the right, replacing one black image column with one newly acquired A-line envelope, which has been assigned to the motion phase of the respective gated M-mode image, at a time. After the end of the display has been reached, the new A-line envelope is plotted onto the first display column replacing the oldest displayed A-line envelope from the history of the respective gated M-mode image, and so forth. This procedure of appending the A-line envelopes to the respective gated M-mode image until the end of the display has been reached, wherein then the next A-line envelope of the respective gated M-mode image is plotted on the first display column, is performed for each of the gated M-mode images, which are temporally consecutively displayed on the display unit for showing the periodic movement of the object.

Referring again to FIG. 2, the catheter tip 6 further comprises an energy application unit 12 being, in this embodiment, an RF ablation electrode for applying energy to the tissue wall 24. The catheter 5 forms therefore a sensing probe, in which the ultrasound transducer 13 and the RF ablation electrode 12 are integrated. The RF ablation electrode 12 is connected with an RF source 22 via an electrical connection 14 like an insulated wire.

The imaging system 1 further comprises a display control unit 20 for controlling a display unit 21 like a monitor. The display control unit 20 is adapted such that the generated ultrasound images are temporally consecutively displayed on the display unit 21 for showing the periodic movement of the tissue wall 24. The resulting shown dynamic, move-like image of the tissue wall 24 and also of the catheter tip 6 allows a user, in particular a physician, to monitor important aspects like the tissue wall thickness, the level of transmurality, the level of gas formation, if present, et cetera, which would be difficult to accurately observe, if a static ungated M-mode image would be used instead of the dynamic image provided by the imaging system 1. The inaccurate observation of these aspects based on a conventional static ungated M-mode image is due to ultrasound imaging disturbances, which will exemplarily be described in the following with reference to FIGS. 7 to 10.

Figure 7:
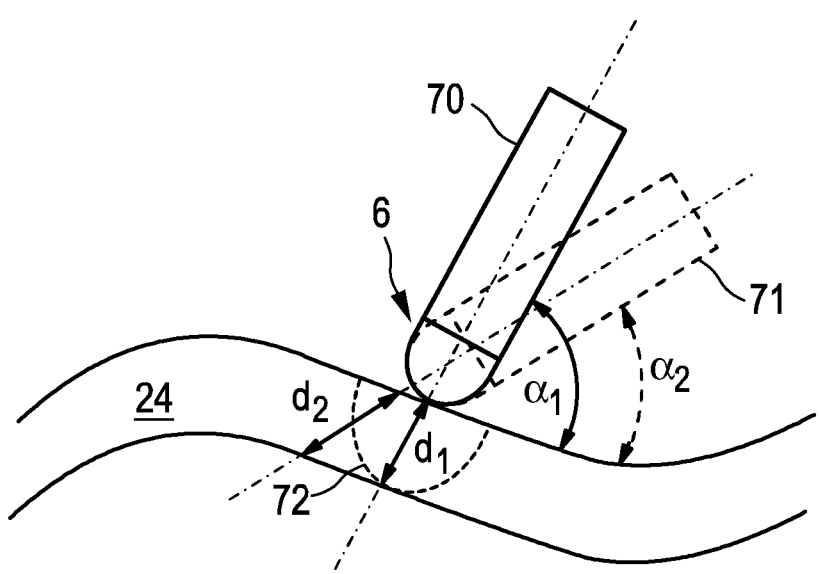
FIGS. 7 to 10 illustrate different kinds of disturbances of ultrasound imaging caused by periodic cardiac and respiratory movements, FIG. 11 exemplarily illustrates the process of generating gated ultrasound images.

FIG. 7 shows the tip 6 of the catheter 5 in two different positions 70, 71, which correspond to two different angles $\alpha_1$, $\alpha_2$, which the catheter tip 6 encloses with the outer surface of the tissue wall 24. Because of the periodic motion of the tissue wall 24 the catheter tip 6 periodically changes between the different positions 70, 71 with respect to the outer surface of the tissue wall 24. As it is clear from FIG. 7, the two thicknesses $d_1$, $d_2$ of the tissue wall 24, which correspond to the two positions 70, 71, are not equal. Correspondingly, also the lesion formation, which is indicated in FIG. 7 by the broken line 72, can be seen to be "deeper" or "less deep" depending on the respective position 70, 71 of the catheter tip 6. These effects lead to the fact that in a known static M-mode image, i.e. an ungated M-mode image not considering the different motion phases, the thickness variation, which may be very rapid, is hard to interpret by a physician and that the physician may judge the thickness to be $d_2$, while in real it is $d_1$. Thus, if the physician would perform the ablation procedure based on a known static M-mode image, the physician may choose a too aggressive ablation regime. Moreover, if the physician monitors the ablation procedure based on a known static M-mode image, the physician may miss the first transmural point such that the ablation may become ineffective and too long, thereby potentially damaging adjacent tissue.

Figure 8:
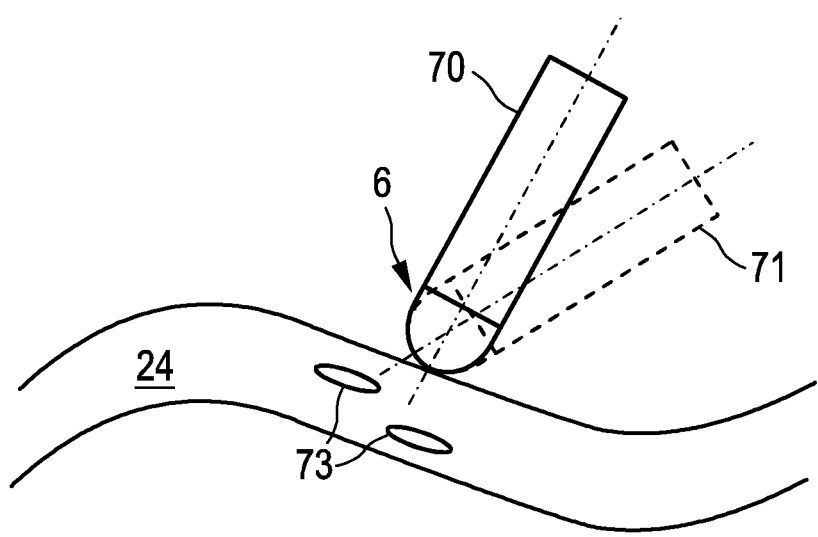

FIG. 8 shows different tissue structure elements 73, which may move in and out of the ultrasound beam provided by the ultrasound transducer 13. In a known static M-mode image this in and out moving of the tissue structure elements 73 would disturb the M-mode image and therefore reduce the visibility of lesion formation.

Figure 9:
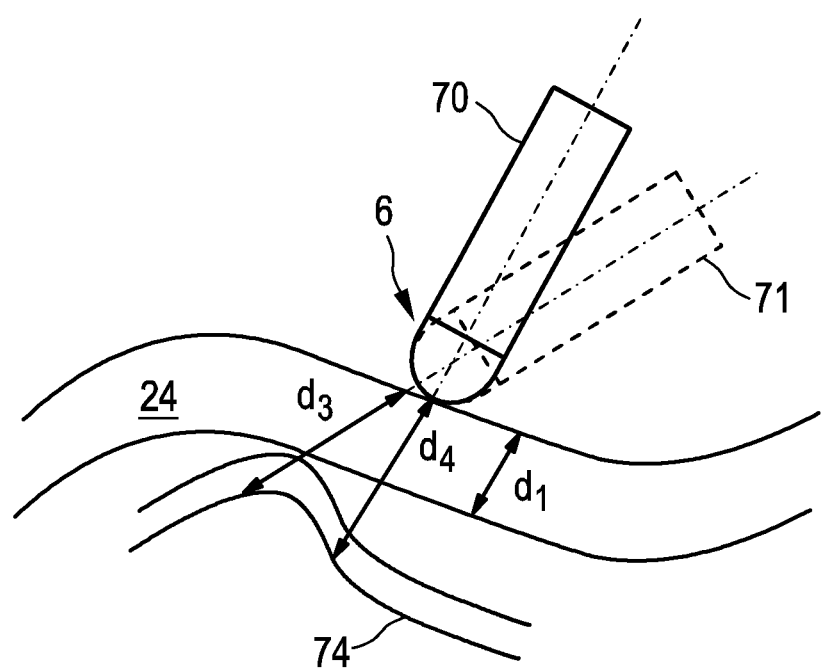

In FIG. 9 a second tissue layer 74 like pericardial sac, lung tissue or a fat layer is shown behind the tissue wall 24. In a known static M-mode image the second tissue layer 74 and the tissue wall 24 may not be separable, because the motion of the tissue wall 24 and the second tissue layer 74 mixes these two elements in the known ungated M-mode image.

For instance, in the example shown in FIG. 9 the distance $d_3$ is equal to the distance $d_4$, wherein the tissue gap along $d_4$, which will be shown as a dark region in the M-mode image, is hard to observe, because a bit later in time, when the catheter tip 6 is positioned along $d_3$, a tissue gap does not exist and the corresponding region in the M-mode image shows up bright. In a known static M-mode image, which covers the long required period of time to see lesion progression of, for instance, 60 seconds, the individual A-lines are plotted so close together that the tissue gaps along $d_4$ cannot be observed. Thus although the actual tissue layer thickness, i.e. the thickness of the tissue wall 24, is $d_1$, the physician may believe that the thickness is equal to $d_3$.

Figure 10:
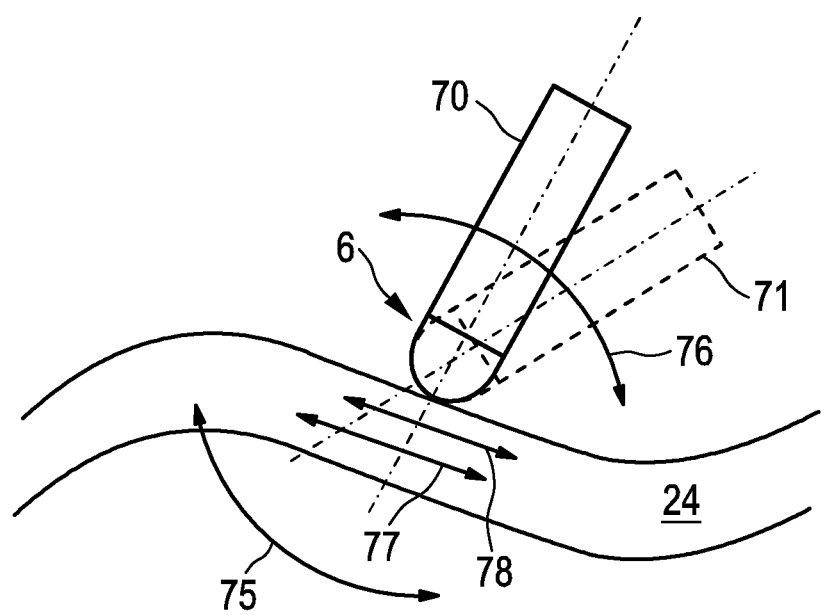

In FIG. 10 motion caused by heart beating and breathing is indicated by arrows 75, 76 and motion caused by locally contracting tissue is indicated by arrows 77, 78. In a known static M-mode image contrast variations in the M-mode image due to the heart beating and breathing motion may interfere with contrast variations due to local muscle contraction. Because of this interference the local muscle contractions cannot be observed in the static M-mode image, although their magnitude difference before and after ablation can be an important indicator of the level of necrosis, in other words an important indicator of how well the ablation procedure went.

The imaging system 1 provides a visualization, in particular, for cardiac ablation monitoring, which solves the above mentioned problems that are related to known static, i.e. ungated, M-mode images of a periodically moving object, wherein the term "periodic" preferentially means that a pattern repeats itself, wherein the pattern repetition frequency does not necessarily need to be constant. The visualization preferentially shows the dynamic M-mode history as a sequence of cardiac gated images instead of a static ungated image. The sequence of gated images can reveal the thickness variations and lesion depth according to FIG. 7, the different structures at different times in the sequence according to FIG. 8, the different tissue structures moving against each other according to FIG. 9 and the local contractibility of heart tissue according to FIG. 10. In particular, by showing N images as a repeating cycle, while the N images are built up in time according to FIG. 6, the user, in particular, the EP physician has a much clearer view on the lesion formation compared to a static ungated conventional M-mode image.

Figure 11:
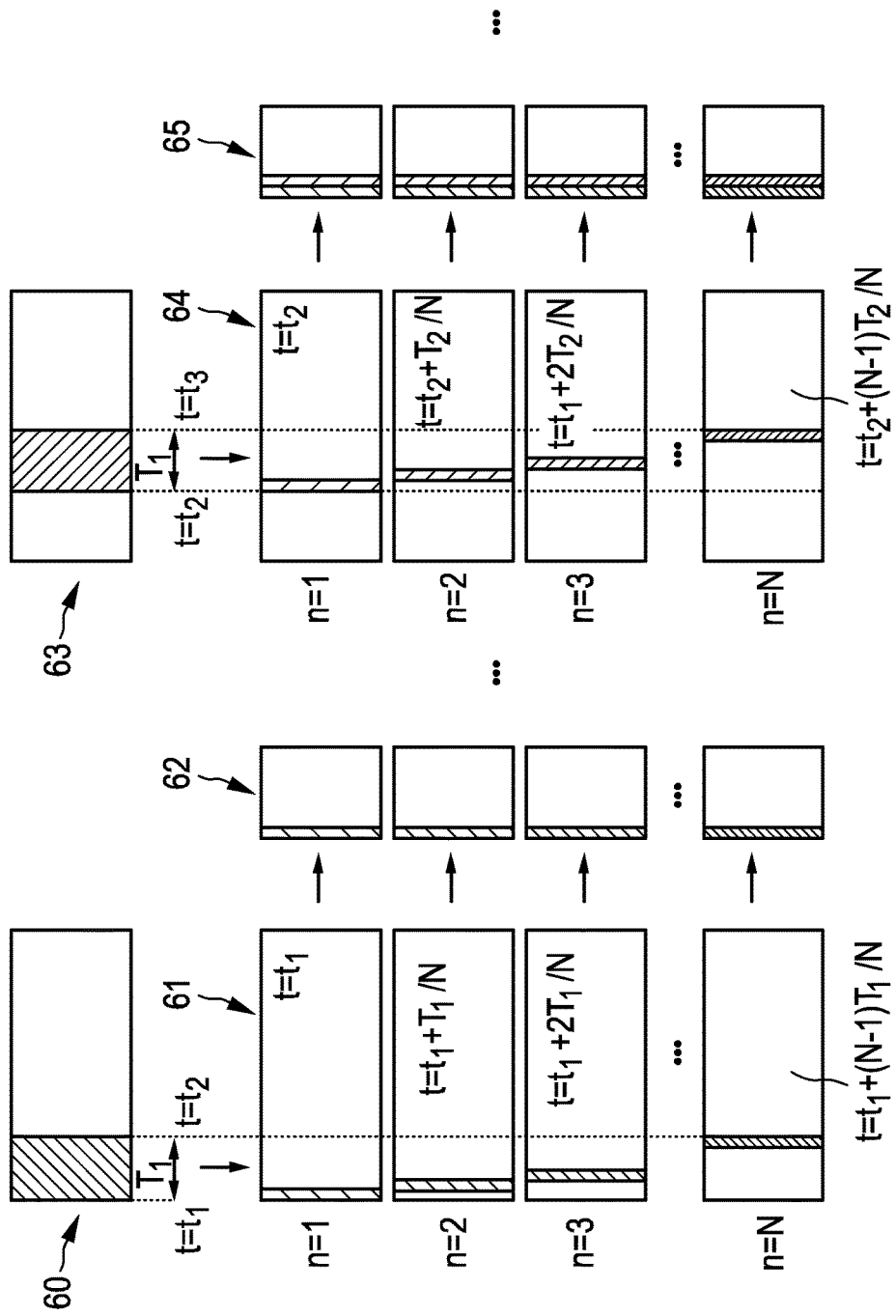

In the following the generation of the dynamic image will exemplarily be illustrated with reference to FIG. 11.

After the first motion period, which in this embodiment is a heart motion period, but which can also be a lung motion period, with a duration of $T_1$ seconds, the ultrasound signals providing unit 13, 16 has provided A-line envelopes 60 belonging to that period. The motion period with the duration $T_1$ is subdivided into N motion phases, wherein each motion phase has a duration of $T_1/N$ seconds. The assigning unit 18 then assigns the provided A-line envelopes to the different moving phases as indicated by the elements 61 in FIG. 11. The ultrasound images generation unit 19 generates N initial M-mode images 62 for the different N motion phases by using the provided A-line envelopes, which have been assigned to the respective motion phase. In this way the provided A-line envelopes belonging to the first motion period are distributed across N gated images, wherein subsequent A-lines, i.e. in this embodiment subsequent A-line envelopes, that span a time period of $T_1/N$ seconds are grouped. The display control unit 20 is adapted to control the display unit 21 such that these N initial gated images are shown as a sequence with a certain video frame rate. Next, after a second motion period of duration $T_2$ seconds further A-line envelopes 63 belonging to the second motion period are provided and assigned to the N motion phases as indicated by the elements 64 shown in FIG. 11, wherein the assigned A-line envelopes are appended to the respective initial M-mode images 62 by the ultrasound images generation unit 19 for generating updated M-mode images 65. Thus, in each gated image the A-line data from a previous iteration is appended with the new A-line data. The display control unit 20 controls the display unit 21 to show the updated N gated images as a sequence with the certain video frame rate. At this point in time the N gated images from the first motion period have been shown on the display unit twice. This process is repeated for each new motion cycle.

The number N of motion phases can be chosen depending on a desired image frame rate and/or a desired lateral resolution of the respective gated M-mode image, wherein for larger values of N the gated image frame rate is proportionally higher and the gated image lateral resolution is proportionally smaller and wherein for smaller values of N the gated image frame rate is proportionally smaller and the gated image lateral resolution is proportionally higher. The imaging system 1 may comprise a user interface for allowing a user to set a desired number N of motion phases directly or indirectly by setting a desired gated image frame rate or a desired gated image lateral resolution.

The imaging system 1 is preferentially adapted to continuously provide ultrasound signals, assign the ultrasound signals to the motion phases, generate the ultrasound images and display the generated ultrasound images, wherein the ultrasound images generation unit 19 is adapted to, after initial ultrasound images have been generated, update the ultrasound images based on the actually provided ultrasound signals and wherein the display control unit 20 is adapted to control the display unit 21 to display the updated ultrasound images temporally consecutively for showing an updated periodic movement of the object 24. In particular, the ultrasound signals providing unit 13, 16 is adapted to continuously provide A-lines, especially A-line envelopes, as the ultrasound signals, wherein the images generation unit 19 is adapted to generate M-mode images as the ultrasound images, wherein, after initial M-modes have been generated, the M-mode images are updated by appending actually provided A-lines and wherein the display control unit 20 is adapted to control the display unit 21 to display the updated M-mode images temporally consecutively for showing an updated periodic movement of the object.

The display control unit 20 is adapted to determine a repetition rate of displaying the generated ultrasound images from the provided phase signal and to control the display unit 21 to display the generated ultrasound images temporally consecutively with the determined repetition rate. The repetition rate preferentially defines how often an ultrasound image of a same motion phase is displayed in a time interval. The resulting frame rate, which can be defined as a total number of images shown in a time interval, is defined by the repetition rate multiplied by the number N of motion phases, for which an ultrasound image has been generated. In this embodiment, the display control unit 20 is adapted to determine a motion rate of the periodic movement of the tissue wall 24 from the provided phase signal and to determine the repetition rate depending on the motion rate. For instance, the repetition rate can be equal to the motion rate, in particular, to the last motion rate as defined by the last motion period, or the repetition rate can be an average of several motion rates defined by several motion periods of the periodic movement. Thus, the video frame rate can be such that N consecutive ultrasound images are shown in a time period T which is equal to one cycle period of the motion, if the motion period is subdivided into N motion phases. Since the repetition rate preferentially depends on the motion rate being, in this embodiment, the heart beat rate, it can vary depending on a variation of the motion rate. For instance, if the heart beat rate increases, also the repetition rate may increase, and, if the heart beat rate decreases, also the repetition rate may decrease.

Thus, the imaging system 1 is preferentially adapted to show a signal history in a periodic dynamic way with a certain video frame rate that is proposed to be chosen such that N consecutive gated images are shown in a time period T which is equal to one cycle period of the motion, wherein preferentially the lastly measured cycle period is used.

Although in the embodiment described above with reference to FIG. 11 the assigning unit 18 subdivides a motion period into motion phases having the same duration, the assigning unit can also be adapted to subdivide a motion period into motion phases such that they have different durations depending on the phase signal. In other words, the N gated M-mode images can have different lateral resolutions. In particular, in this embodiment certain motion phases of a heart beat cycle may last shorter, which leads to fewer A-lines, than other motion phases of the same heart beat cycle. For instance, the assigning unit can be adapted such that the duration of a motion phase including the diastole, where the heart muscles are at rest, is larger than the duration of a motion phase including the systole.

In an embodiment the ultrasound signals providing unit is adapted to provide A-lines as the ultrasound signals, the assigning unit is adapted to assign the A-lines to the motion phases based on the provided phase signal, and the images generation unit is adapted to generate M-mode images for the different motion phases as the ultrasound images based on the respective assigned A-lines, wherein the width of the A-lines of at least one motion phase is modified such that for different motion phases the width of the A-lines used for generating the respective M-mode image is similar. Thus, the images generation unit can be adapted to re-scale a group of A-lines belonging to a certain motion phase, in order to match the size of a group of A-lines belonging to the other motion phases, so that all motion phases end up to produce the same amount of appended data in the gated M-mode images. Such a resizing ensures that the different gated M-mode images have the same size such that, if the gated M-mode images are displayed temporally consecutively on the display unit for showing the periodic movement of the object, a flickering of the shown movement caused by differently sized gated M-mode images can be prevented. For modifying the width of the A-lines a bi-linear resizing procedure or any other image scaling method can be used.

A position detection system 7 can be used to detect the position of the tip 6 of the catheter 5 within the person 2. In this embodiment the position detection system 7 is an x-ray fluoroscopy system, in particular, an x-ray C-arm system. The x-ray fluoroscopy system comprises an x-ray source 8 for generating x-rays 9 which traverse the person 2 on the table 3, wherein the x-rays 9, which have traversed the person 2, are detected by an x-ray detector 10. The x-ray fluoroscopy system 7 further comprises a fluoroscopy control unit 11 for controlling the x-ray source 8 and the x-ray detector 10. The x-ray detector 10 generates x-ray images of the person 2, which can be shown on the display unit 21. On the generated x-ray images the tip 6 of the catheter 5 is visible within the person 2 such that the x-ray images show the position of the tip 6 of the catheter 5 within the person 2. In other embodiments other position detection systems for detecting the position of the catheter tip within the person can be used like position detection systems which are based on electromagnetic sensors, ultrasound sensors, et cetera.

The imaging system 1 further comprises a navigation unit 23 for allowing the catheter 5, in particular, the catheter tip 6, to be navigated to a desired location within the person 2. The navigation unit 23 can be adapted to allow a user to navigate the catheter 5 completely by hand or semi-automatically. The catheter 5 comprises built-in guiding means (not shown in FIG. 1), which can be controlled by the navigation unit 23. The catheter 5 can, for example, be steered and navigated by the use of steering wires, in order to guide the catheter tip 6 to a desired location within the person 2.

Figure 12:
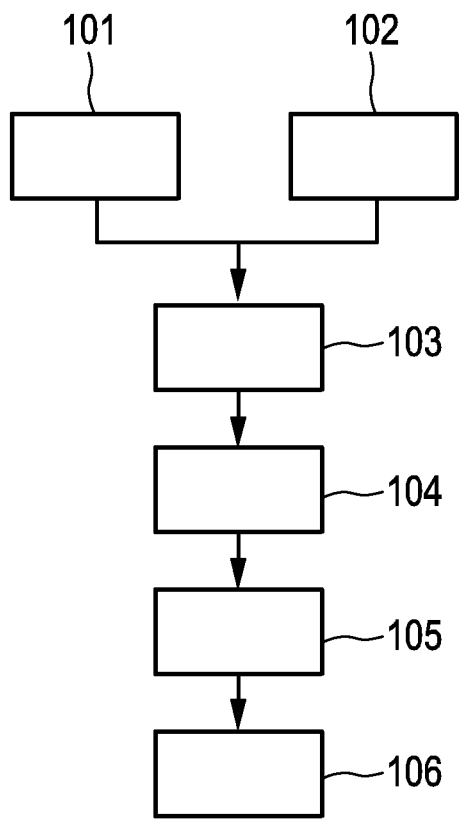
FIG. 12 shows a flowchart exemplarily illustrating an embodiment of an imaging method for imaging a periodically moving object.

In the following an embodiment of an imaging method for imaging a periodically moving object will exemplarily be described with reference to a flowchart shown in FIG. 12.

In step 101 ultrasound signals of the object are provided for different times by an ultrasound signals providing unit. In particular, the ultrasound signals providing unit acquires A-lines, pre-filters the A-lines for removing noise and applies an envelope detection algorithm on the pre-filtered A-lines for generating A-line envelopes as the ultrasound signals. In step 102 a phase signal being indicative of motion phases of a periodic movement of the object at the different times is provided by a phase signal providing unit. For instance, a cardiac signal being indicative of a cardiac motion of the object at the different times, for which the A-lines have been provided, is provided as the phase signal. In step 103 the ultrasound signals are assigned to the motion phases based on the provided phase signal by an assigning unit. Preferentially, the provided A-line envelopes are assigned to different cardiac phases based on the cardiac signal. In step 104 several ultrasound images are generated for the different motion phases by an ultrasound images generation unit, wherein an ultrasound image for a motion phase is generated based on the ultrasound signals assigned to the respective motion phase. For instance, each A-line envelope, which has been assigned to a certain motion phase, is used for generating an M-mode image for this certain motion phase. Thus, if a new A-line envelope has been provided and assigned to a certain motion phase, this A-line envelope can be appended to the respective M-mode image of the respective motion phase. In step 105 a display unit is controlled by a display control unit, wherein the control is performed such that the generated ultrasound images are temporally consecutively displayed on the display unit for showing the periodic movement of the object.

Steps 101 to 105 can be performed continuously such that continuously ultrasound signals, in particular A-lines, more specifically A-line envelopes, are generated, assigned to the respective motion phase and appended to the respective M-mode image for continuously updating the M-mode images, which are generated for the different motion phases, and such that the continuously updated M-mode images are continuously temporally consecutively displayed on the display unit for showing the actually updated periodic movement of the object.

The imaging system and the imaging method provide an alternative way of visualizing an M-mode image to solve the problem of motion distortions, wherein the periodic nature of the motion is exploited. Preferentially, an M-mode image is gated resulting in several gated images, each corresponding to one motion phase of a motion cycle, wherein these gated images are visualized as a motion sequence, in particular in realtime. This allows a user like a physician to, for instance, interpret heart tissue-catheter interaction and to easily perceive relevant heart wall parameters like the local wall thickness, lesion formation, local tissue contractibility and tissue-catheter interaction/contact.

The imaging system preferentially comprises an ultrasound transducer mounted inside a catheter for ultrasound imaging inside a body of a person. The imaging system is preferentially adapted to monitor cardiac ablation, which is preferentially performed for curing certain arrhythmia. The imaging system therefore preferentially comprises a catheter with an ablation electrode and an ultrasound transducer in its tip, in order to enable a physician in an EP laboratory to assess almost in realtime certain relevant parameters of a heart wall from the inside. By visual inspection of the displayed motion sequence the physician may measure the heart wall thickness and decide on the best ablation regime, i.e. the physician may set the ablation power, the flow rate of fluid cooling and the ablation duration based on the observed heart wall thickness. Moreover, the physician can monitor the lesion formation while ablating and halt the ablation when a lesion has become transmural, i.e. when the treatment has reached the backside of the heart wall. In case steam pocket is formed inside the heart tissue, the physician can see this on the display unit and can halt the ablation, in order to prevent tissue rupture, i.e. a so-called "pop".

Generally, one of the N gated images will be better compared to the others for the visualization of a certain aspect of the cardiac wall. For instance, one of the N gated images will be associated with the minimum observed wall thickness of the tissue wall of the heart as exemplarily described above with reference to FIG. 7, which expectactly is the actual wall thickness. Thus, one of the N gated images will generally be the optimal one for a certain aspect and another gated image of the same sequence may be optimal for another aspect. The imaging system visualizes the N gated images as a moving sequence which repeats itself such that a user like a physician can see all aspects in a short time frame. Thus, the user may observe different aspects simultaneously based on the displayed dynamic, movie-like periodic movement of the tissue wall, i.e. based on the moving visualization of the N gated images.

Although in the above described embodiments the phase signal providing unit is preferentially adapted to provide a single phase signal being particularly a cardiac trigger signal, the phase signal providing unit can also be adapted to provide several phase signals being indicative of motion phases of different kinds of periodic movements of the object, wherein in this case the assigning unit can be adapted to assign the ultrasound signals to a combination of motion phases of the different kinds of periodic movements based on the provided several phase signals, wherein the ultrasound images generation unit can be adapted to generate several ultrasound images for the different combinations, wherein an ultrasound image for a combination is generated based on the ultrasound signals assigned to the respective combination. For instance, one particular gated image, which has been gated in accordance with a first trigger signal, can be again subdivided into double-gated images on the basis of another trigger signal. In particular, in such a cascade of image gating firstly a heart beat motion artifact can be removed and secondly a breathing motion artifact can be removed or vice versa.

Although in the above described embodiments certain trigger signals have been described as phase signals, in other embodiments also other phase signals can be provided for determining motion phases. For instance, the phase signal providing unit can be adapted to provide at least one of an atrium motion signal being indicative of atrium motion and a ventricle motion signal being indicative of ventricle motion. In particular, in the case of atrium fibrillation, in which the atrium contracts with a higher frequency than the ventricle, firstly the atrium motion artifact may be removed by using a first trigger signal that is synchronous with the atrium motion and secondly the ventricle motion artifact may be removed using a second trigger signal that is synchronous with the ventricle motion or vice versa. Moreover, also more than two phase signals can be provided. For instance, three types of motion artifacts can be removed in any order by a successive application of gating with different appropriate trigger signals like an atrium beating trigger signal, a ventricle beating trigger signal and a breathing motion trigger signal.

Although in the embodiment described above with reference to FIG. 2 the catheter tip comprises a single ultrasound transducer only, in another embodiment the catheter tip can also comprise two or more ultrasound transducers. Preferentially, different ultrasound transducers can acquire different A-lines, which can be used for generating different sets of gated M-mode images, which can be shown in a moving sequence on the display unit, i.e., for instance, for each set of gated M-mode images a dynamic, movie-like image of the periodic motion can be shown by displaying the respective gated M-mode images temporally consecutively.

Procedures, which have been desribed above with respect to A-lines, can also be performed with A-line envelopes and vice versa.

Although in the above described embodiments the imaging system and the imaging method are adapted to image a tissue wall of a heart of a person, in other embodiments the imaging system and the imaging method can also be adapted to image another periodically moving object like another periodically moving tissue structure of a person or of an animal or like a periodically moving technical object.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like assigning procedures for assigning a motion phase to a provided ultrasound signal, ultrasound images generation procedures for generating ultrasound images based on the ultrasound signals, displaying procedures for displaying the generated ultrasound images temporally consecutively, et cetera performed by one or several units or devices can be performed by any other number of units or devices. For instance, steps 103 to 105 can be performed by a single unit or by any other number of different units. The procedures and/or the control of the imaging system in accordance with the imaging method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an imaging system for imaging a periodically moving object. An assigning unit assigns ultrasound signals like A-lines to motion phases based on a provided phase signal, wherein an ultrasound images generation unit generates several ultrasound images like gated M-mode images for the different motion phases based on the ultrasound signals assigned to the respective motion phase. The ultrasound images are temporally consecutively displayed on a display unit for showing the periodic movement of the object. The resulting dynamic, movie-like image of the object allows a user like a physician to more reliably determine properties of the object like a thickness of a tissue wall, in particular, during an ablation procedure. The imaging system is therefore particularly useful for monitoring cardiac ablation procedures.

The invention claimed is:

1. An imaging system for imaging a periodically moving object, the imaging system comprising:
   an ultrasound signals providing unit for providing ultrasound signals of the object for different times,
   a phase signal providing unit for providing a phase signal indicative of repetitive motion periods corresponding to a periodic movement of the object according to a repeating cycle;
   an assigning unit for dividing the motion periods into motion phases within the motion periods and assigning the ultrasound signals to the motion phases in the motion periods, based on the provided phase signal;
   an ultrasound images generation unit for generating ultrasound images for the motion phases, respectively, based on the ultrasound signals assigned to the respective motion phases; and
   a display controller for controlling a display, such that the generated ultrasound images are temporally consecutively displayed on the display for showing the periodic movement of the object,
   wherein the ultrasound signals providing unit is adapted to temporally consecutively provide A-lines as the ultrasound signals; wherein the images generation unit is adapted to generate M-mode images as the ultrasound images and to update the M-mode images generated for the motion phases in the motion periods by appending actually provided A-lines, which have been assigned to the respective motion phases, to the respective M-mode images, and wherein the display controller is adapted to control the display to display the updated M-mode images temporally consecutively for showing an updated periodic movement of the object.

2. The imaging system as defined in claim 1, wherein the display controller is adapted to determine a repetition rate of displaying the generated ultrasound images from the provided phase signal based on the repetitive motion periods, and to control the display to display the generated ultrasound images temporally consecutively with the determined repetition rate.

3. The imaging system as defined in claim 2, wherein the display controller is adapted to determine a motion rate of the periodic movement of the object, as defined by a last motion period of the repetitive motion periods, from the provided phase signal and to determine the repetition rate depending on the motion rate.

4. The imaging system as defined in claim 1, wherein the assigning unit is adapted to subdivide each motion period into the motion phases such that they have different durations depending on the phase signal.

5. The imaging system as defined in claim 4, wherein the assigning unit is adapted to assign A-lines to each of the motion phases based on the provided phase signal, the images generation unit is adapted to generate M-mode images for the motion phases as the ultrasound images based on the respective assigned A-lines, wherein a collective width of the A-lines of at least one motion phase is modified such that for different motion phases the respective collective width of the A-lines used for generating the respective M-mode image is similar.

6. The imaging system as defined in claim 1, wherein the assigning unit is adapted to assign the ultrasound signals of a current motion period of the object to the motion phases of the current motion period based on the motion phases of a temporally previous motion period, as indicated by the phase signal.

7. The imaging system as defined in claim 6, wherein the assigning unit is adapted to reassign the ultrasound signals of a respective motion period of the object, which have been assigned to the motion phases based on the phase signal for a previous motion period, based on the phase signal of the respective motion period, after the respective motion period has been completed, wherein the ultrasound images generation unit is adapted to generate the ultrasound images based on the reassigned ultrasound signals and wherein the display controller is adapted to control the display to display the generated ultrasound images.

8. The imaging system as defined in claim 1, wherein the phase signal providing unit is adapted to provide the phase signals indicative of motion phases of different kinds of periodic movements of the object, wherein the assigning unit is adapted to assign the ultrasound signals to a combination of motion phases of the different kinds of periodic movements based on the provided phase signals, wherein the ultrasound images generation unit is adapted to generate ultrasound images for different combinations of motion phases, and wherein an ultrasound image for each combination is generated based on the ultrasound signals assigned to the respective combination.

9. The imaging system as defined in claim 1, wherein the object is a region of a living being and wherein the phase signal providing unit is adapted to provide at least one of a cardiac motion signal being indicative of cardiac motion and a respiratory motion signal being indicative of respiratory motion as the phase signal.

10. The imaging system as defined in claim 1, wherein the imaged object is a region of a living being and wherein the phase signal providing unit is adapted to provide at least one of an atrium motion signal being indicative of atrium motion and a ventricle motion signal being indicative of ventricle motion as the phase signal.

11. The imaging system as defined in claim 1, wherein the phase signal providing unit is further adapted to determine the phase signal from the ultrasound signals and to provide the determined phase signal.

12. The imaging system as defined in claim 1, wherein a video frame rate of the display provides N consecutive ultrasound images in a time period, which is equal to one cycle period of the repeating cycle when the motion period is subdivided into N motion phases.

13. An imaging method for imaging a periodically moving object, the imaging method comprising:
providing ultrasound signals of the object for different times;
providing a phase signal indicative of repetitive motion periods corresponding to a periodic movement of the object, according to a repeating cycle;
dividing each of the motion periods into motion phases;
assigning the ultrasound signals to the motion phases in the motion periods based on the provided phase signal;
generating ultrasound images for the motion phases in the motion periods, respectively, based on the ultrasound signals assigned to the respective motion phases; and
controlling a display by a display controller, such that the generated ultrasound images are temporally consecutively displayed on the display for showing the periodic movement of the object,
wherein A-lines are temporally consecutively provided as the ultrasound signals, wherein M-mode images are generated as the ultrasound images for the motion phases in the motion periods and are updated by appending actually provided A-lines, which have been assigned to the respective motion phases, to the respective M-mode images, and wherein the updated M-mode images are displayed on the display temporally consecutively for showing an updated periodic movement of the object.

14. A non-transitory computer readable medium having stored thereon a program that, when executed by a computer, causes the computer to image a periodically moving object by:
receiving ultrasound signals of the object for different times, wherein A-lines are temporally consecutively received as the ultrasound signals;
receiving a phase signal, the phase signal being indicative of repetitive motion periods corresponding to a periodic movement of the object according to a repeating cycle;
dividing each of the motion periods into motion phases of the periodic movement of the object and assigning the ultrasound signals to the motion phases in each of the motion periods, respectively, based on the received phase signal;
generating ultrasound images for the motion phases in the motion periods, respectively, based on the ultrasound signals assigned to the respective motion phases, wherein M-mode images are generated as the ultrasound images for the motion phases in the motion periods and are updated by appending actually provided A-lines, which have been assigned to the respective motion phases, to the respective M-mode images; and
causing the generated ultrasound images to be temporally consecutively displayed on a display for showing the periodic movement of the object, wherein the updated M-mode images are displayed on the display temporally consecutively for showing an updated periodic movement of the object.

* * * * *